United States Patent [19]

Sadeghi et al.

[11] Patent Number: 5,258,708
[45] Date of Patent: Nov. 2, 1993

[54] METHODS AND APPARATUS FOR NON-DESTRUCTIVE TESTING OF MATERIALS WITH EDDY CURRENTS

[75] Inventors: Seyed H. H. Sadeghi; Dariush Mirshekar-Syahkal, both of Colchester, England

[73] Assignee: University of Essex, Colchester, United Kingdom

[21] Appl. No.: 715,110

[22] Filed: Jun. 12, 1991

[51] Int. Cl.$^5$ .................... G01N 27/87; G01N 27/90
[52] U.S. Cl. ............................ 324/240; 324/718; 324/715; 324/262; 324/225
[58] Field of Search ............... 324/225, 226, 227, 236, 324/239-243, 260-263, 713, 715, 716, 709, 609, 718

[56] References Cited

U.S. PATENT DOCUMENTS

| Re. 21,853 | 7/1941 | Atkinson | 324/716 |
|---|---|---|---|
| 2,200,827 | 5/1940 | Atkinson | 324/716 |
| 2,351,201 | 6/1944 | Gillis | 324/716 |
| 3,617,874 | 11/1971 | Forster | 324/263 X |
| 3,875,502 | 4/1975 | Neumaier | 324/242 X |
| 4,218,651 | 8/1980 | Ivy | 324/262 X |
| 4,266,185 | 5/1981 | Charlesworth et al. | 324/718 |
| 4,303,883 | 12/1981 | Mori et al. | 324/243 X |
| 4,510,447 | 4/1985 | Moyer | 324/240 X |
| 4,677,379 | 6/1987 | Arnaud et al. | 324/242 |
| 4,683,419 | 7/1987 | Neuelmann et al. | 324/263 X |
| 4,706,021 | 11/1987 | Chamuel | 324/242 |
| 4,983,158 | 1/1991 | Nakata et al. | 324/263 |

OTHER PUBLICATIONS

Ceccs et al, "Recognizing the Scope of Eddy Current Testing", *Research Techniques in Nondesctructive Testing*, vol. VIII, (R. S. Sharpe ed.), no month 1985, pp. 270-300.

Moulder et al, "Uniform Field Eddy Current Probe: Experiments and Inversion for Realistic Flaws", *Rev. Prog. in Quantitative N.D. Evaluation*, vol. 6, no month 1987, pp. 601-610.

Moulder et al, "Progress in Uniform Field Eddy Current Methods", *Rev. Progress in Quantative Non Destructive Evaluation*, vol. 7, no month 1988, pp. 147-155.

Capobianco et al, "Standard Flaws for Eddy Current Probe Characterization," *Rev. Progress in Quantitative Non-Destructive Evaluation*, vol. 8, no month 1989, pp. 985-999.

Primary Examiner—Gerard R. Strecker
Assistant Examiner—Warren S. Edmonds
Attorney, Agent, or Firm—Synnestvedt & Lechner

[57] ABSTRACT

In a non-destructive method for the detection of surface cracks in metals, an eddy current is induced in the surface region of a workpiece under test, at a frequency sufficiently high to generate an alternating magnetic field solely in the skin region of the workpiece. That alternating surface magnetic field is interrogated by means of a relatively small electro-magnetic induction sensor, having regard to the overall area of the induced magnetic field. The sensor provides a voltage output which is analysed, preferably in real time, to yield an indication sensor. Also described is a probe for performing such a method.

6 Claims, 13 Drawing Sheets

METHODS AND APPARATUS FOR NON-DESTRUCTIVE TESTING OF MATERIALS WITH EDDY CURRENTS

BACKGROUND TO THE INVENTION (a) Field of the Invention

This invention concerns the non-destructive testing metals, and in particular relates to a method for detecting surface cracks in metals, as well as to a probe adapted for use in such a method.

(b) Description of the Prior Art

Surface cracks in metals can arise from a number of causes, but most notably as a consequence of fatigue. Particularly in the aircraft industry, the non-destructive testing of metals to determine the presence of such surface cracks has assumed great importance, and an eddy current method of testing has been under extensive investigation for some time now (as described for example in Cecco, V. S. and Van Drunen, G in *Research Techniques in Nondestructive Testing*, vol. 8, Academic Press, 1985). In such methods, an eddy current is induced in the surface region of the metal under test and the crack is detected by observing the effect that the crack has on the induced eddy current. In these, a coil is disposed above the metal surface and an alternating current passed through that coil, so as to induce an eddy current in the skin region of the metal under test. The inducing coil serves as the primary of a transformer, with the metal under test serving as the secondary of that transformer; if then the eddy currents in the metal under test are affected by the presence of one or more cracks, there is a consequential change in impedance in the primary coil. By detecting and analysing the changes in impedance, it is possible to derive not only the presence but also the size of any cracks in the surface of the workpiece.

A disadvantage with the above eddy current techniques is that the quantitative measurement of surface cracks requires complicated calibration procedures, often involving the use of certain calibration standards, as described for example in the above-mentioned article and also in articles in *Review of Progress in Quantitative Nondestructive Evaluation*—and specifically pp. 601–610, volume 6, 1987; pp.147–155, volume 7, 1988; and pp. 985–989, volume 8, 1989.

The known eddy current techniques are performed by taking a series of measurements over the surface of the metal under test, storing the results of each measurement, and then processing all of the results so as to obtain data indicative of both the presence and sizes of cracks. Though the use of high speed computer techniques allows rapid analysis, nevertheless these techniques cannot be performed in real time and in any event are relatively complicated to perform and process, especially if the area of the workpiece is relatively large.

OBJECTS OF THE INVENTION

This invention extends from research into the known eddy current techniques, with the object of obtaining a non-destructive metal-testing technique which may operate in real time, and so give an instantaneous indication of at least the presence of any surface cracks in a workpiece under test.

It is a further object to provide a non-destructive technique for use on metals and which will yield the size of any surface cracks determined as being present.

Yet another object is to provide a non-destructive crack-detection technique which an easily be performed on metal components without necessarily having to remove those components from service. Such a technique may be used for example on aircraft components to great advantage.

A further object of this invention is to furnish a probe for use in a real-time crack-detection technique on metal components which does not itself damage the components.

SUMMARY OF THE INVENTION

In accordance with the foregoing and other objects, this invention in one aspect provides a non-destructive method for the detection of surface cracks in metals, in which method a non-uniform eddy current is induced in a metal workpiece under test, the frequency of the eddy current being sufficiently high to have that eddy current essentially only in the surface region of the workpiece under test the consequent alternating surface magnetic field is interrogated by means of a magnetic field sensor, which sensor provides a voltage output and the voltage output is analysed to yield an indication in the event of the presence of a crack in the vicinity of the sensor.

A second aspect of the present invention provides a probe for use in a non-destructive testing method for surface cracks in a metal workpiece, which probe comprises a main frame, a pair of generally U-shaped inducer wires lying in parallel spaced-apart planes and supported by said main frame, at least two legs to support said main frame at a predetermined height above a workpiece surface with the lower portions of each of said two inducer wires extending substantially parallel to said surface, and a magnetic sensor attached to one of said legs and disposed to lie closely adjacent to the workpiece surface for interrogating a magnetic field induced substantially in the surface of the workpiece by said inducer wires.

It will be appreciated that in the eddy current method of the present invention, referred to hereinafter as a surface magnetic field measurement (SMFM) technique, no account is taken of a change in the impedance of the inducing coil, as a consequence of cracks in the metal surface. Instead, reliance is placed on detecting variations in the magnetic field arising from the eddy currents induced in the workpiece, which variations are dependent upon the presence of cracks in the metal surface.

It has been found that not only can the presence of cracks be detected by the method of this invention, but so also can the sizes of any such cracks be determined. This is because the induced eddy currents are also affected by the sizes of such cracks as are present, and so too is the resultant magnetic field; appropriate analysis of the signal obtained by interrogating that magnetic field thus allows the sizes of the cracks also to be determined.

BRIEF DESCRIPTION OF THE DRAWINGS

In order that the invention may better be understood, it will now be described in greater detail and certain specific examples thereof given, reference being made as appropriate to the accompanying drawings, in which.

DESCRIPTION OF THE PREFERRED EMBODIMENT

Figure 1:
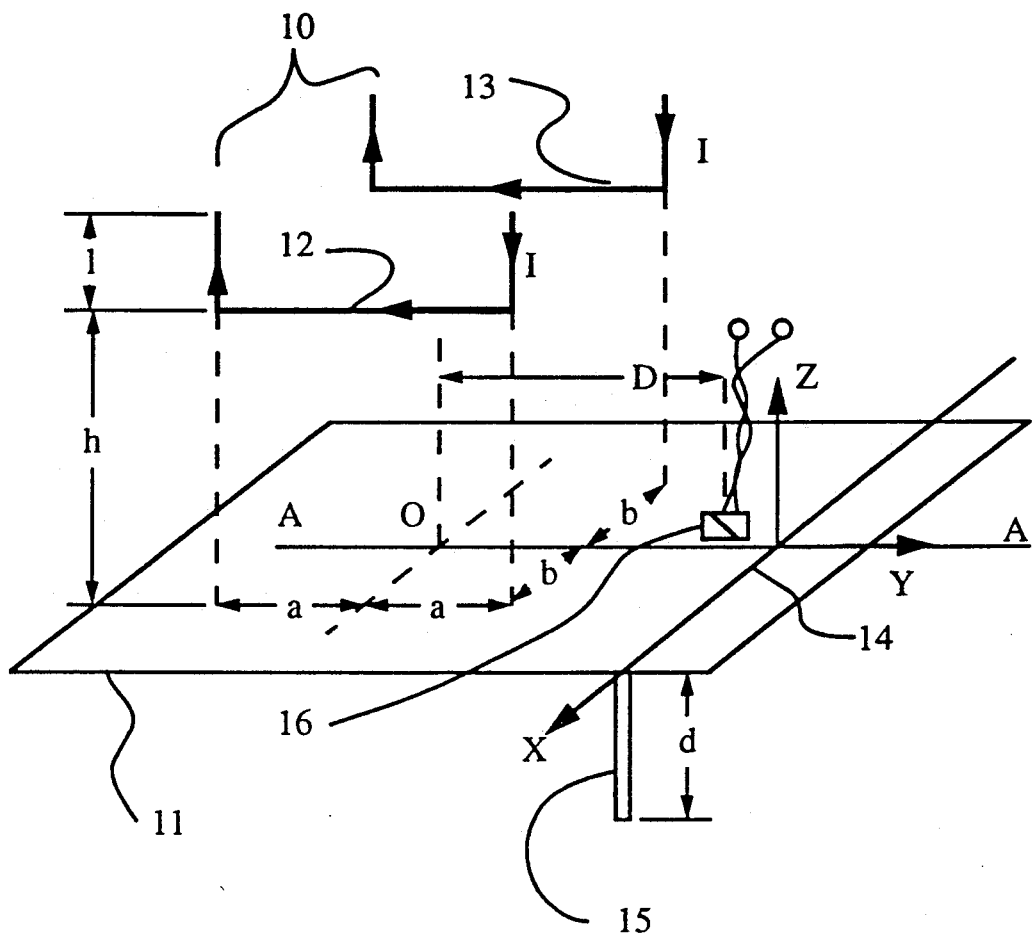
FIG. 1 diagrammatically shows the testing method of this invention.

In order to perform the method of this invention, the sensor preferably has a physical size enabling it to be located very close to the surface of the workpiece, in order to interrogate a relatively small area of the overall induced magnetic field. To this end, the sensor may be somewhat similar to an electro-magnetic recording or playback head for a conventional tape recorder. Alternatively, a sensor including a coil intended for disposition with its axis parallel to the metal surface may be employed.

The eddy current may be induced in the skin region of the workpiece by one of a number of techniques, but preferably are induced by means of an inducer having two U-shaped wires disposed parallel one to another and carrying an alternating current at an appropriate high frequency. Other possible configurations include a rectangular or circular coil consisting of several turns of wires. The frequency of the inducing current should be sufficient to ensure that the eddy currents lie substantially in the skin region of the workpiece. The actual frequency depends upon a number of factors including the permeability and conductivity of the metal under test and the likely depths of the cracks.

In the method of this invention, any surface crack present will produce a sudden discontinuity in the distribution of the surface magnetic field resulting from the induced eddy current. The magnitude of this discontinuity depends upon the crack depth, the shape and dimensions of the inducer, the separation of the inducer from the metal surface and its distance from the crack. For long uniform cracks, it has been found that two measurements of the surface magnetic field are normally sufficient for a determination of the crack depth. Thus, as compared with the known eddy current techniques, the method of this invention offers several advantages including ease of use, simplicity and rapidity in both crack detection and sizing. Specifically, no complex calibration procedures are required and moreover the method may be performed in real time, giving instantaneous indications of the presence and size of cracks.

The method of this invention may be performed by positioning the eddy current inducer at an arbitrary position above the workpiece and then moving the sensor as required within the region in which the eddy current is induced. In the alternative, the sensor and the inducer may be coupled together in some fixed relative disposition, whereby the sensor and inducer are moved together as a probe unit. In this latter case, the induced field is not stationary and varies in accordance with the movement of the probe.

Turning now to the probe itself, each of the legs thereof may be resiliently mounted on the frame, to facilitate the smooth traversing of a workpiece by the probe. Moreover, the end of each leg which contacts the workpiece preferably is ball-shaped, again to facilitate the traversing of the surface of the workpiece, which might include welds, joints and so on.

Though the sensor could be provided within a housing suitably attached to one of the legs, it is preferred for the sensor to be included within one of the legs, at or adjacent the free end thereof. To this end, and where the legs are ball-ended, it is convenient for the sensor to be located wholly within one such ball end.

The probe defined above can be modified so as to be suitable for use in a known testing method for surface cracks in metals, which method is known as an alternating current field measurement (ACFM) technique. Such a technique is described for example in Dover, W. D. et al, in *Eddy Current Characterisation of Metals and Structure*, ASTM 1981.

As a consequence, such a probe for use in an ACFM non-destructive testing method for surface cracks of metals, may comprise a main frame, a pair of U-shaped inducer wires lying in parallel spaced apart planes and supported by the frame, two sensing legs which also support the frame at a predetermined height above the workpiece surface with the lower portions of each of the two inducer wires substantially parallel to that surface, and a compensating coil disposed between and electrically coupled in series with the two legs so that the voltage induced in the coil is in antiphase with the voltage induced in the area bounded by the ACFM sensor legs and the metal surface.

Advantageously, the two probes of this invention may be combined into a single unit employing a common frame, legs and a pair of U-shaped inducer wires. The sensor which interrogates the magnetic field may then be employed to perform an assessment of any cracks in the metal, using the SMFM technique. The ACFM technique is able to demonstrate enhanced sensitivity for crack sizing, but is unreliable unless good contact is established between the legs and the metal surface. As a consequence, the two assessments may be compared for greater reliability. Certain specific embodiments will now be described in detail, reference being made to the accompanying drawings as necessary.

Referring initially to FIG. 1, a two wire U-shaped inducer 10 located above the surface of a workpiece 11 is illustrated. As shown in this Figure, the lower parts of the two inducer wires 12 and 13 are parallel to the workpiece surface and may be normal to a crack edge 14. These are not, however, necessary conditions but they facilitate the interpretation of the signal resulting from the presence of a crack 15. The inducer 10 is excited by an alternating current source the frequency of which is selected such that the eddy current produced in the workpiece is essentially confined to the surface. The smaller the current skin depth, the better is likely to be the agreement between the predicted crack depth and the actual crack depth. The magnitude of the current source may vary depending upon the circumstances and the type of sensor used, but typically may be 1A.

Figure 2:
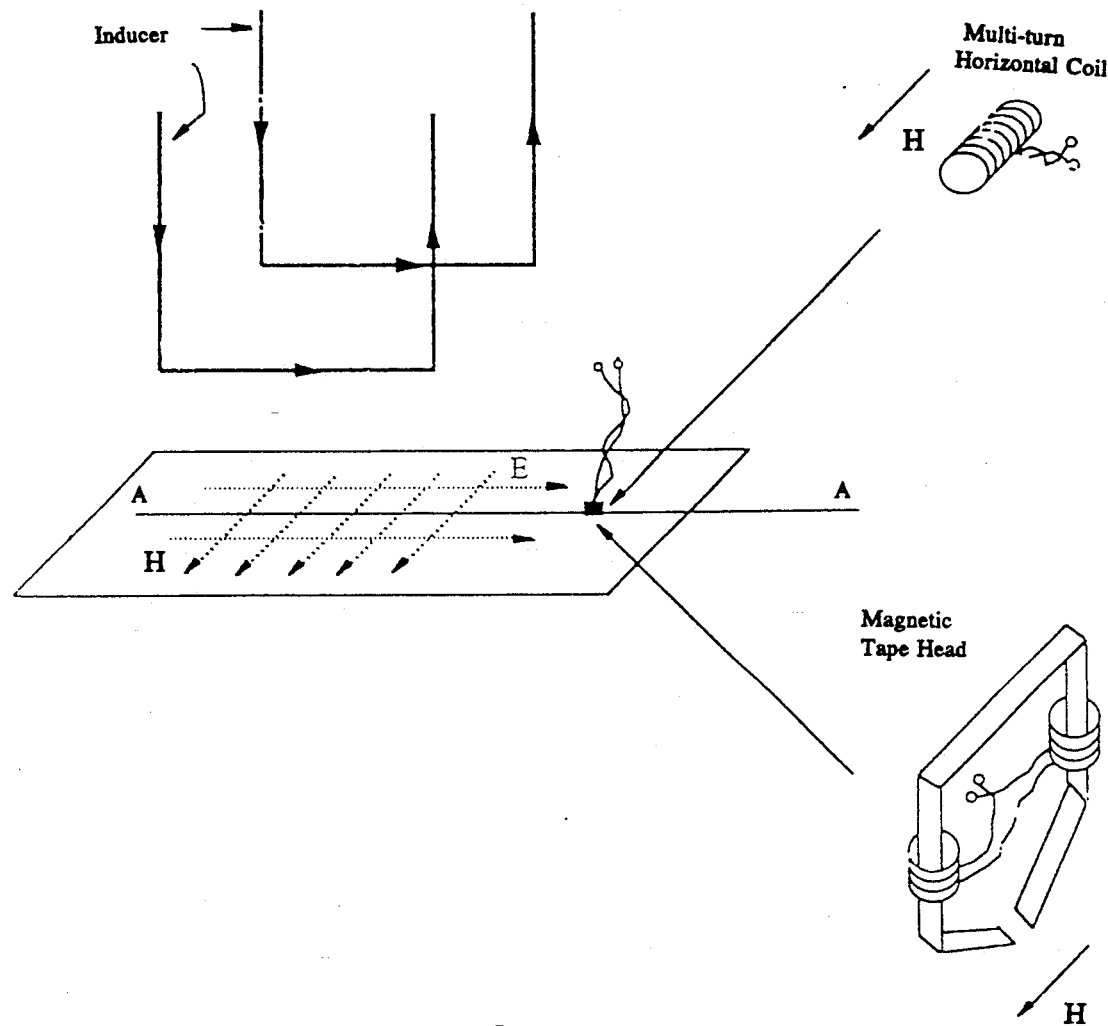
FIG. 2 shows the orientation of a sensor with respect to an inducer performing the method.

In performing a method of this invention where the inducer is held stationary, the a magnetic field detecting sensor 16 is moved along line A—A, lying in the plane of symmetry of the inducer, parallel to the wires. The orientation of the sensor 16 is set such that the sensor samples the magnetic field component normal to line A—A. The sensor itself may be similar to a magnetic tape head or may be a horizontal coil, and FIG. 2 shows the correct orientation of these with respect to the inducer.

FIG. 3 shows the results of performing the SMFM technique of this invention on a mild steel block containing saw-cut notches of 2 mm, 3 mm, 8 mm and 10 mm in depth, simulating long surface cracks. The dimensions of the inducer were a=25 mm, b=5 mm, l=120 mm and the lift-off distance h=37 mm (referring to FIG. 1), and the frequency of the inducing current I was at 1.6 kHz, giving a skin depth in mild steel of approximately 0.2 mm.

Figure 3A:
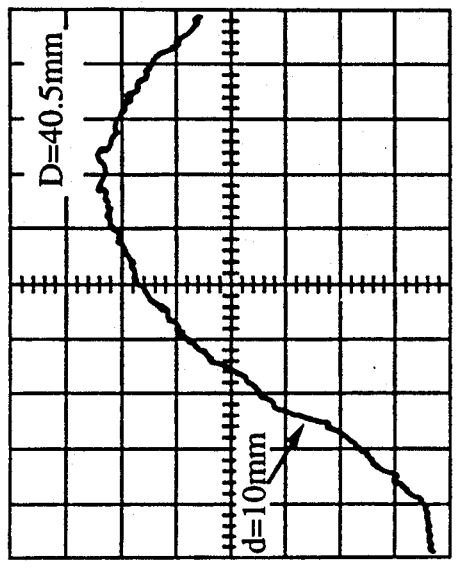
FIGS. 3(a)-(d) show results obtained by performing the method of this invention.
Figure 3B:
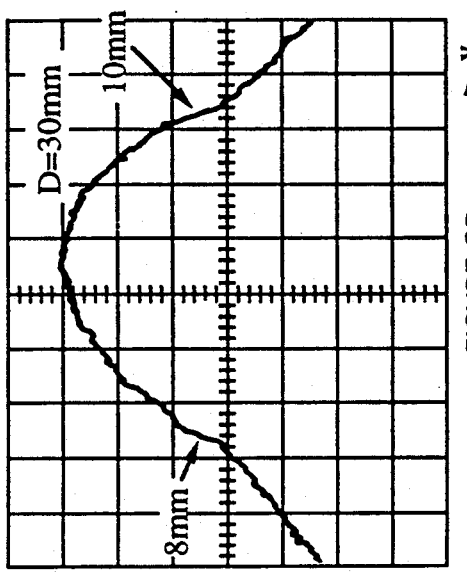
Figure 3C:
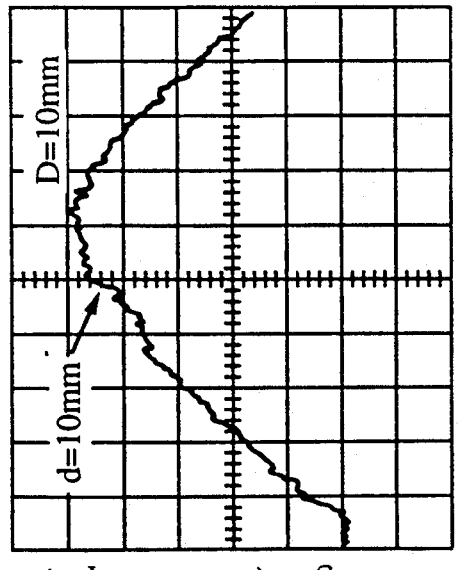
Figure 3D:
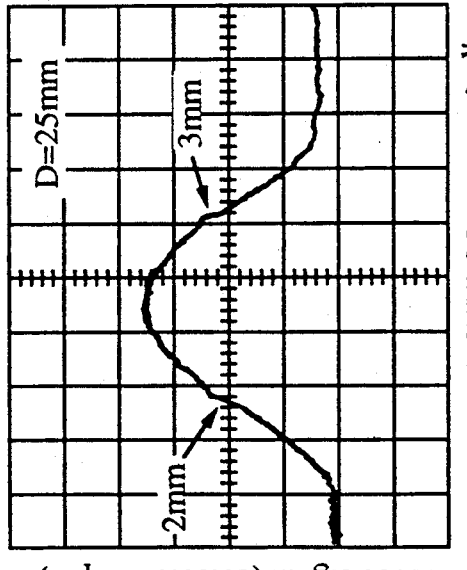

FIGS. 3a and 3b show results with the inducer at two different positions with respect to the 10 mm notch, and the discontinuity in the surface magnetic field and its dependence upon the inducer position can clearly be seen. FIG. 3c shows the case where the inducer was located symmetrically between the 2 mm and 3 mm notches and FIG. 3d the case where the inducer was located symmetrically between the 8 mm and 10 mm notches. These results demonstrate the effects of two notches of different depths on the induced surface magnetic field.

Figure 4:
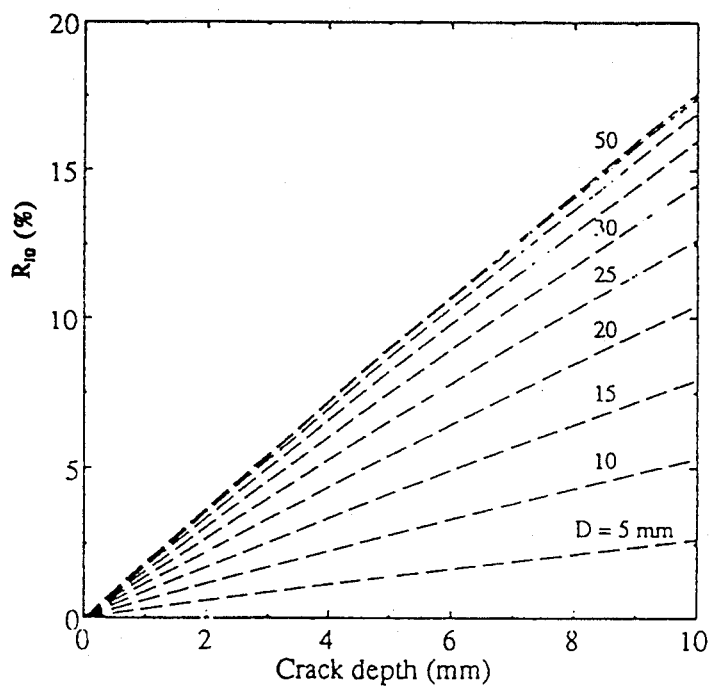
FIG. 4 is a set of curves generated for use with the probe of FIG. 1.

The set of curves shown in FIG. 4 have been generated for inverting the signal from the sensor, for a long surface crack. The ordinate of the chart represents a change in the magnetic field relative to the lowest value of the magnetic field at the edge of a crack, and parameter D represents the distance between the crack edge and the centre of the inducer. Similar curves for other U-shaped inducers can be generated using a computer programme based on a theoretical model assuming one dimensional cracks and negligible current skin depth. This theoretical model can then be further extended to includes two dimensional cracks and inducers of other configurations. With the aid of the curves provided in FIG. 4, the discontinuities shown in FIG. 3 were inverted to give the depths of the notches. These measured depths and the actual depths are shown in Table 1 below. The errors quoted in the table are typical for an SMFM technique and can be attributed to the edge effect and the distance of the sensor for the workpiece, neither of which are accommodated in the computer model.

TABLE 1

| d (actual depth) (mm) | $d_m$ (measured depth) (mm) | $d_m - d$ (%) |
|---|---|---|
| 2.0 | 2.35 | +17.5 |

TABLE 1-continued

| d (actual depth) (mm) | $d_m$ (measured depth) (mm) | $d_m - d$ (%) |
|---|---|---|
| 3.0 | 3.47 | +15.8 |
| 8.0 | 7.06 | −11.8 |
| 10.0 | 10.36 | +3.6 |

Figure 5:
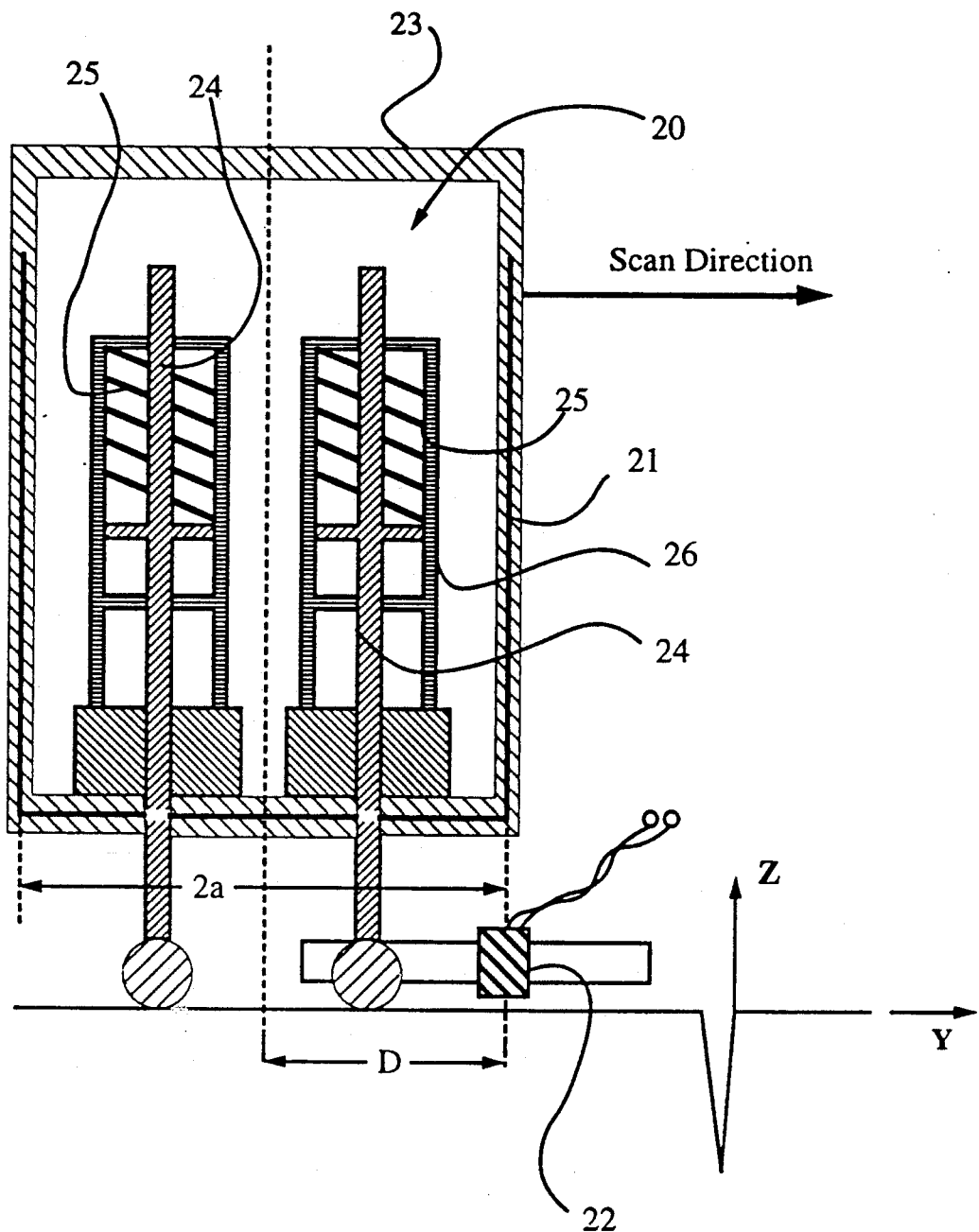
FIG. 5 shows diagrammatically a practical embodiment of a probe for performing the method of this invention.

FIG. 5 shows diagrammatically a probe 20 including an inducer 21 and sensor 22, integrated into one unit. The sensor is attached to the inducer along the Y axis (FIG. 1) at an arbitrary measuring point located D from the centre of the inducer. Again, the sensor has to be disposed very close to the metal surface. The probe 20 has a Perspex (clear acrylic plastic) casing 23 in which are mounted two legs 24 each of which is spring-loaded downwardly by a respective spring 25 carried in an acetal housing 26. Only one of the two wires of the inducing mechanism is shown at 21. The sensor 22 may take the form of a horizontal coil or a magnetic tape head.

Figure 7:
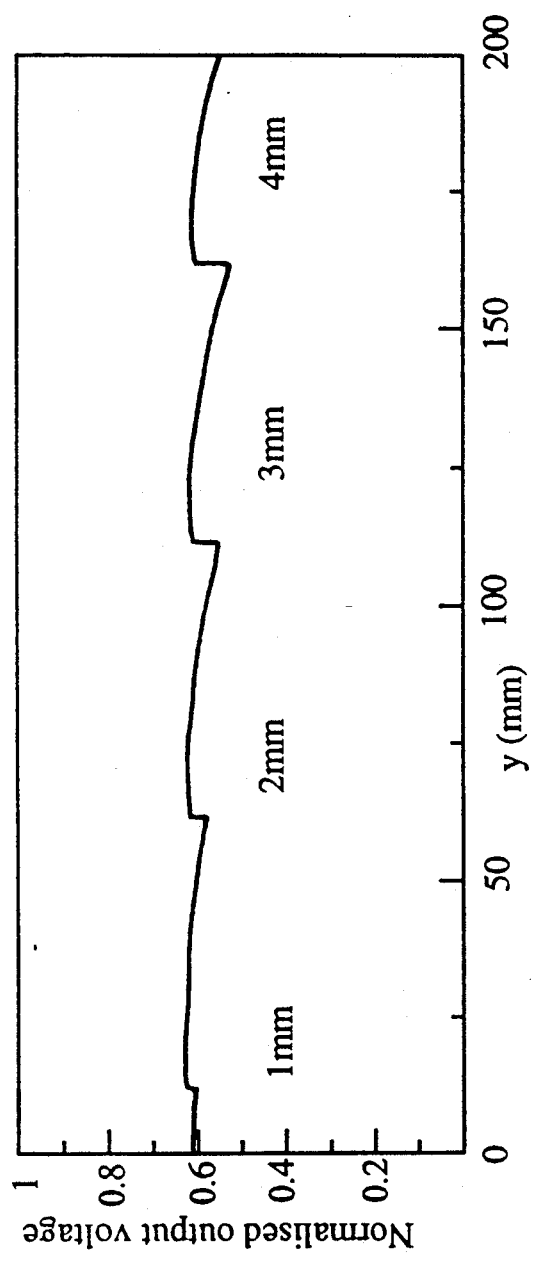
FIGS. 6 and 7 respectively show experimental and theoretical results for experiments performed with the probe of FIG. 5.
Figure 6:
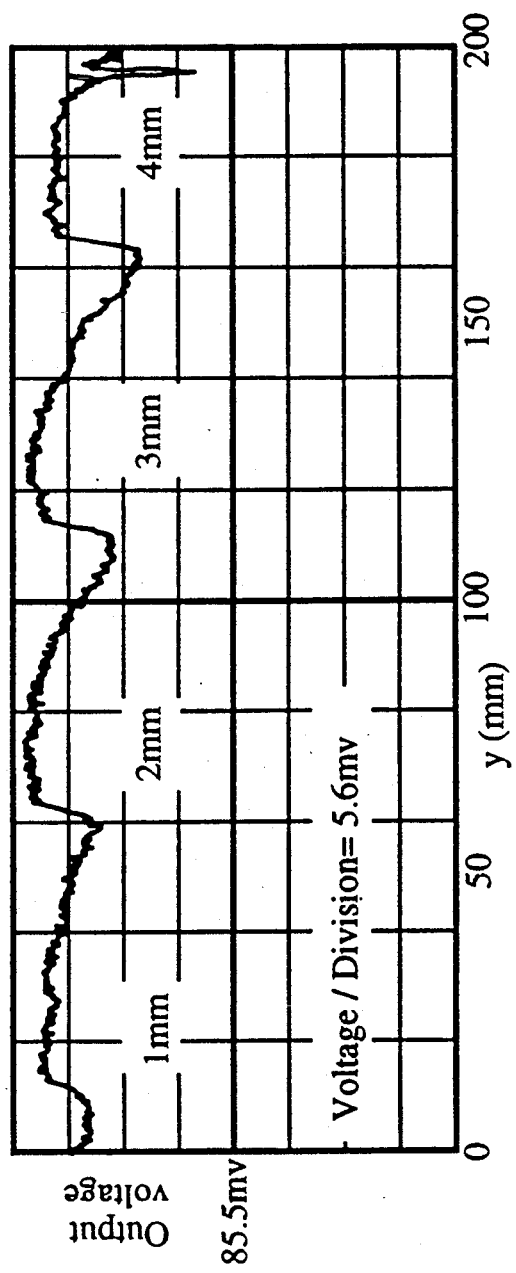

FIG. 6 shows the result of scanning a mild steel test block with theprobe of FIG. 5, with the block containing saw-cut notches of 1 mm, 2 mm, 3 mm and 4 mm depths, at a spacing of 50 mm and simulating long surface cracks. In this experiment, the dimensions of the inducer were a=24 mm, b=5 mm, l=62 mm, the lift-off distance h=15 mm and D=27 mm (FIGS. 1 and 5). A current of 0.4 amps was supplied to the inducer, at a frequency of 1.6 kHz and the sensor output was provided to a phase-sensitive detector. FIG. 7 shows theoretical results corresponding to the above experiment, obtained from the computer model and it can be seen that both the theory and the experiment show the discontinuous nature of the surface magnetic field at the edges of the notches.

Figure 8:
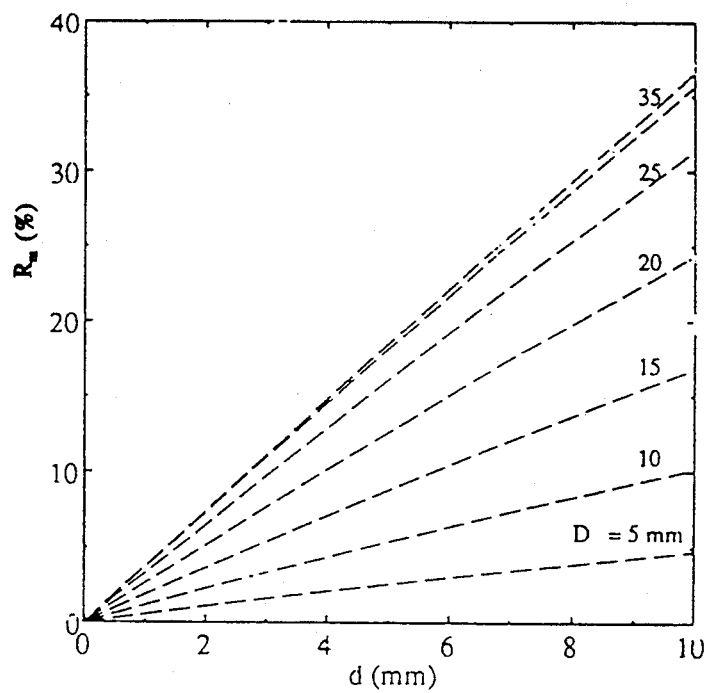
FIG. 8 is a set of curves computed for use with the probe of FIG. 5.

To invert the signal associated with each notch, to provide a notch depth, a set of curves shown in FIG. 8 were computed for the specific inducer. FIG. 8 is therefore similar to FIG. 4 above. Table 2 shows the results of inverting the signals associated with the notches, together with the actual depth and a good agreement between the measured depth and the actual depth is evident.

TABLE 2

| d (actual depth) (mm) | $d_m$ (measured depth) (mm) | $(d_m - d)/d$ (%) |
|---|---|---|
| 1.02 | 1.00 | −2 |
| 2.01 | 1.93 | −4 |
| 3.00 | 2.48 | −5.3 |
| 3.96 | 3.50 | −11.6 |

Figures 9, 9A:
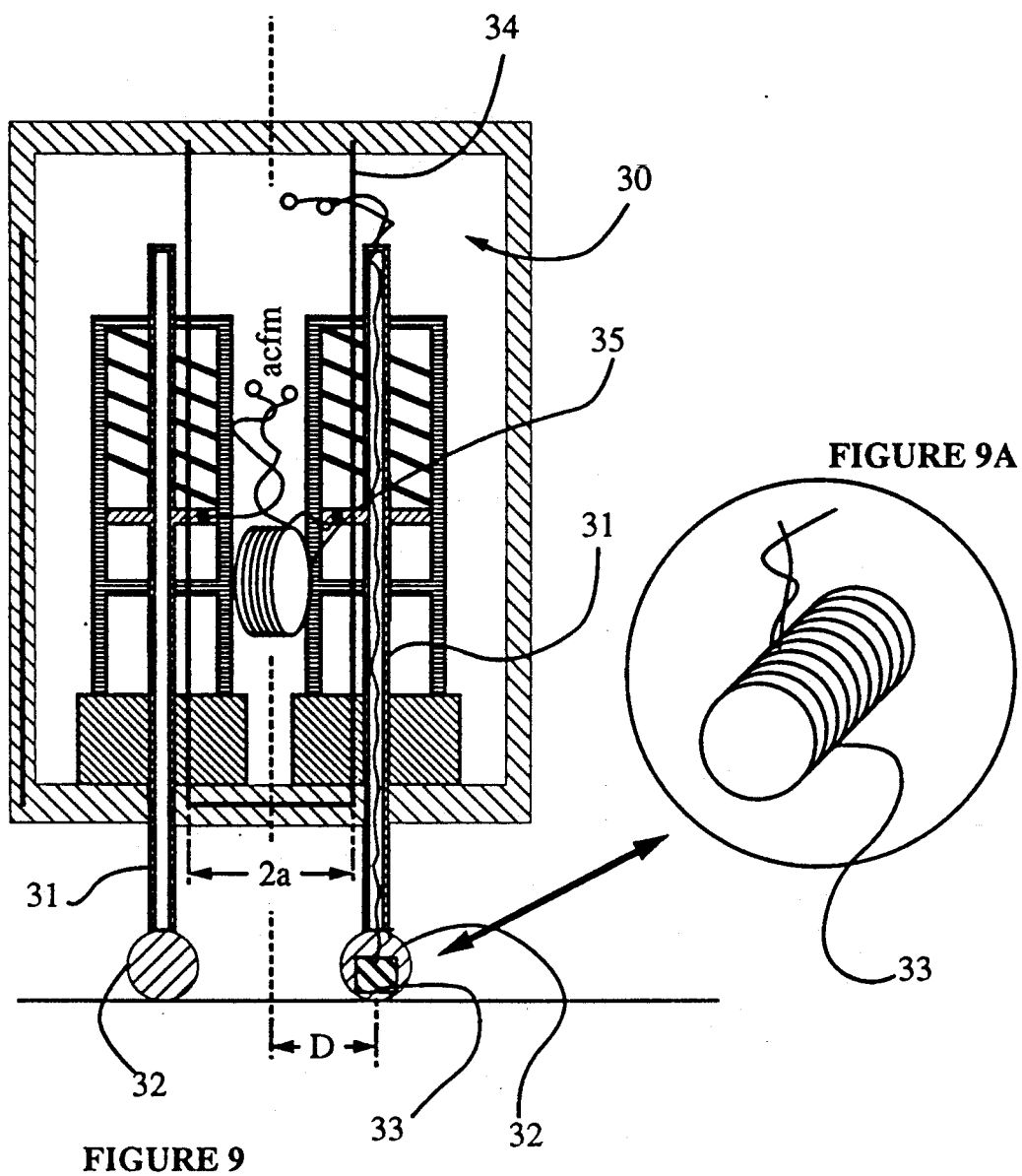
FIGS. 9 and 9A show a modified form of probe assembly, for use both with the method of this invention and as an ACFM sensor.

FIGS. 9 and 9A show diagrammatically a probe somewhat similar to that described with reference to FIG. 5, but modified so as to be suitable for performing an ACFM measuring technique in addition to the SMFM technique of this invention. The probe thus includes two separate sensors, one for each measuring technique, and the legs 31 of the probe are spring loaded in order to maintain the tips in good contact with the workpiece.

The ACFM technique is well established for the detection and sizing of cracks in metals. A two leg sensor is applied to the surface of the workpiece in order to sample the surface potential distribution produced by injecting or inducing a high frequency current into the workpiece. The operating frequency is usually selected so that the current and the consequent field in the workpiece are confined to the metal surface. Ideally, in both the SMFM and ACFM techniques, the skin depth is zero. In the ACFM technique, the current distribution in the absence of any cracks should be uniform and though this is not essential, it simplifies the inversion of the crack signal to produce the crack depth. All work so far reporting the ACFM technique has aimed at producing a uniform surface field.

The integrated probe of FIG. 9 does not produce a uniform surface electric and magnetic field and so the techniques which assume a uniform distribution are not suitable for the inversion of crack signals picked up by the ACFM sensor of the probe of FIG. 9. The computer modelling mentioned above in connection with the SMFM technique can, however, be used to determine the surface electric field from the surface magnetic field and subsequently to obtain multipliers (correction factors) for inverting the ACFM crack signals when using the uniform current distribution inversion formula:

$$d_m = (\Delta/2)(V_2 - V_1)/V_1$$

In the above formula, $d_m$ is the measured crack depth, is the distance between the two tips of the ACFM probe and $V_1$ and $V_2$ are voltages picked up by the probe when applied at the two edges of the crack.

Each leg 31 of the probe of FIG. 9 has a ball end 32 of part spherical shape and the SMFM sensor comprises a small coil 33 housed in one of those ball ends. The probe legs and ball ends are made of stainless steel, which is electrically a low-conductive alloy. It has been found experimentally that at the intended operating frequency (1.6 kHz), this alloy does not have a significant screening effect nor does it have considerable perturbing effect on the magnetic field produced by the inducer.

In a specific embodiment of probe, the SMFM sensor comprised 100 turns of enamelled wire of 50 um diameter wound on a 2 mm long optical fibre of 1 mm diameter. The complete coil measured 2 mm diameter by 2 mm long, and was located in a probe foot of 4 mm radius but including a bore of 2.6 mm to accommodate the coil. When the coil was properly located in the foot, its centre was not about 1.4 mm from the workpiece surface. The leg supporting the coil was hollow and a pair of twisted wires was passed through that leg to carry the coil signal.

The ACFM sensor utilises the probe legs, which are relatively long. When the integrated probe is located on a workpiece, the magnetic field from the inducer including wire 34 cuts the area formed between the two legs of the ACFM sensor and the workpiece. As a result, a strong extraneous voltage is generated at the output of the ACFM sensor. If not removed, this voltage together with other parasitic voltages give rise to an appreciable residual AC voltage at the output of the phase sensitive detector used for detecting signals from the probe, so reducing the resolution of the ACFM technique. Use of a phase-sensitive detector with a high time constant should alleviate the problem, but this has proved to be impractical due to limitations on the time constant and the saturation of the front-end amplifier of the detector.

Figure 10:
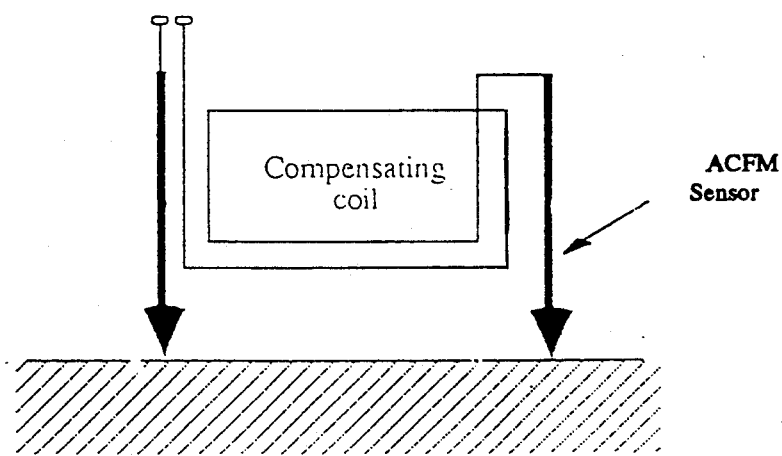
FIG. 10 shows, diagrammatically the arrangement of an ACFM sensor and compensating coil.

In the probe described above, the effect of these voltages has been reduced by providing a relatively large flat coil 35 connected in series with the output of the ACFM sensor, located between the two probe legs 31 so that the voltage induced into the coil 35 is in anti-phase with the voltage induced in the ACFM sensor. Such a compensating coil is shown diagrammatically in FIG. 10. The exact position of the coil and its orientation must be determined experimentally.

Figure 11:
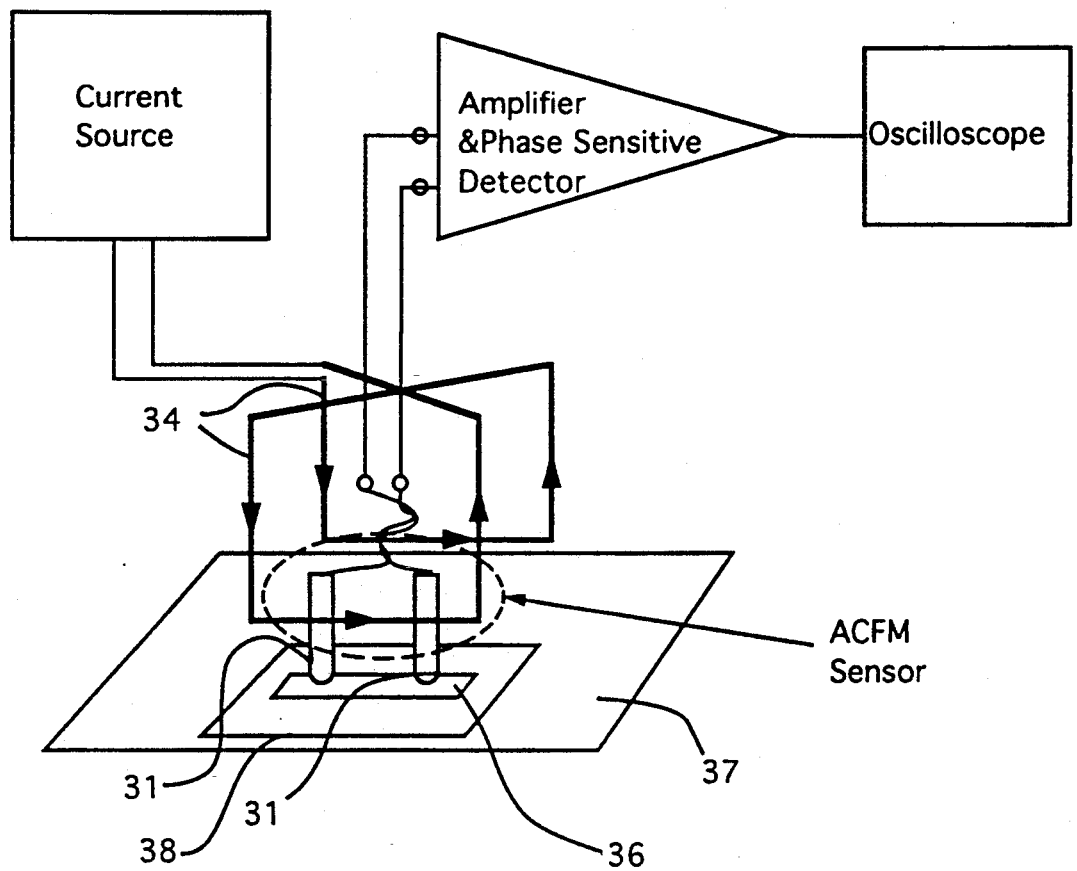
FIG. 11 shows the arrangement for setting up an ACFM sensor of this invention.
Figure 12B:
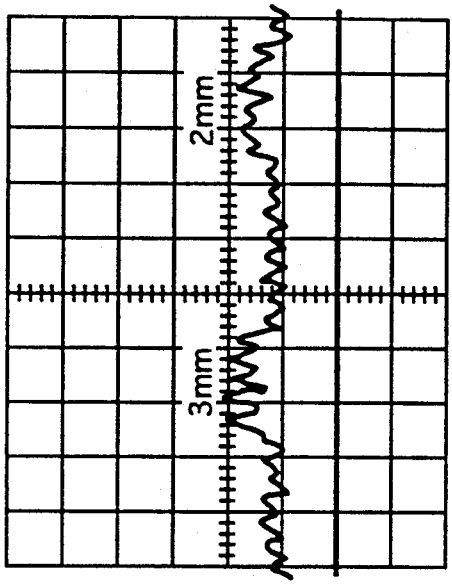
FIGS. 12(a) to (c) show results obtained with an ACFM sensor without a compensating coil and FIG. 12(d) with such a compensating coil.
Figure 12D:
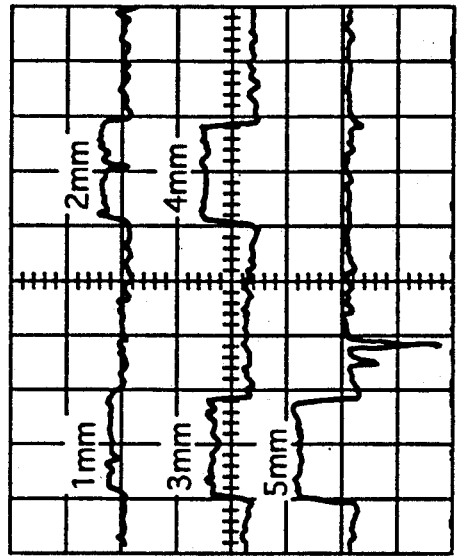
Figure 12A:
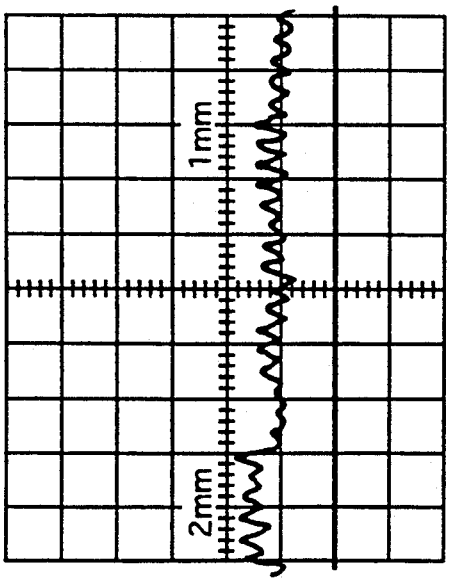
Figure 12C:
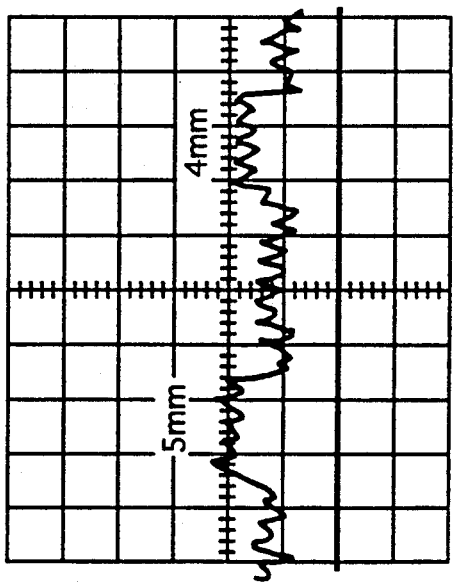

FIG. 11 shows diagrammatically the arrangement for setting up the ACFM sensing system, where the two legs 31 of the probe are applied to a narrow thin copper foil 36 located on the workpiece 37 but separated therefrom by a very thin insulating layer, such as a piece of paper. The position of the compensating coil can then be adjusted to obtain a minimum value for the signal at the output of the front end amplifier of the detector, as monitored by an oscilloscope.

Figure 13:
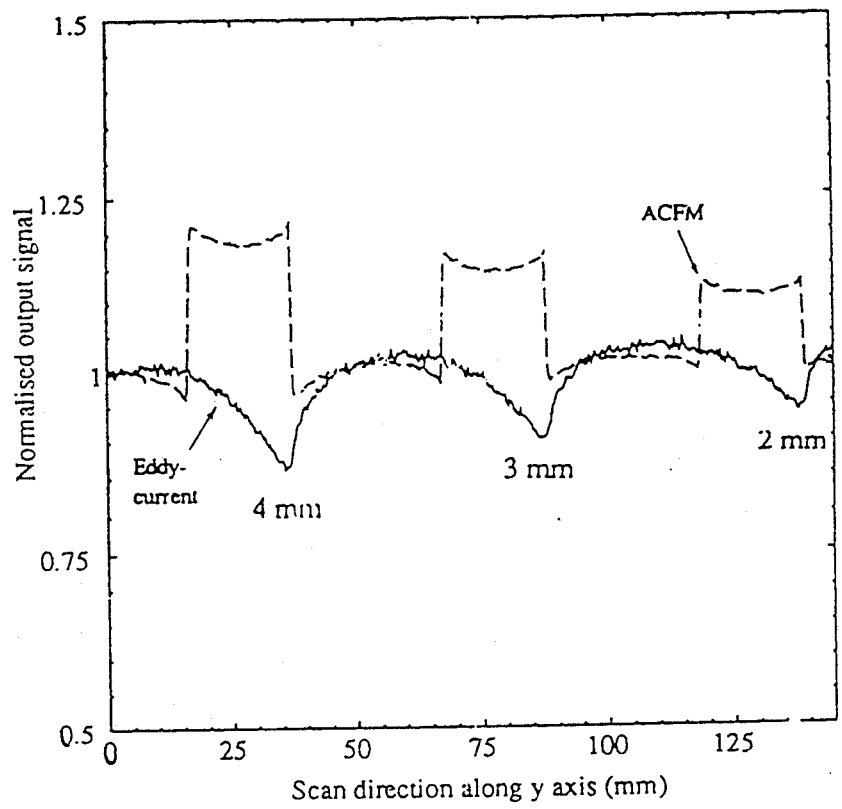
FIG. 13 shows typical signals from combined ACFM and SMFM probes of this invention.
Figure 14:
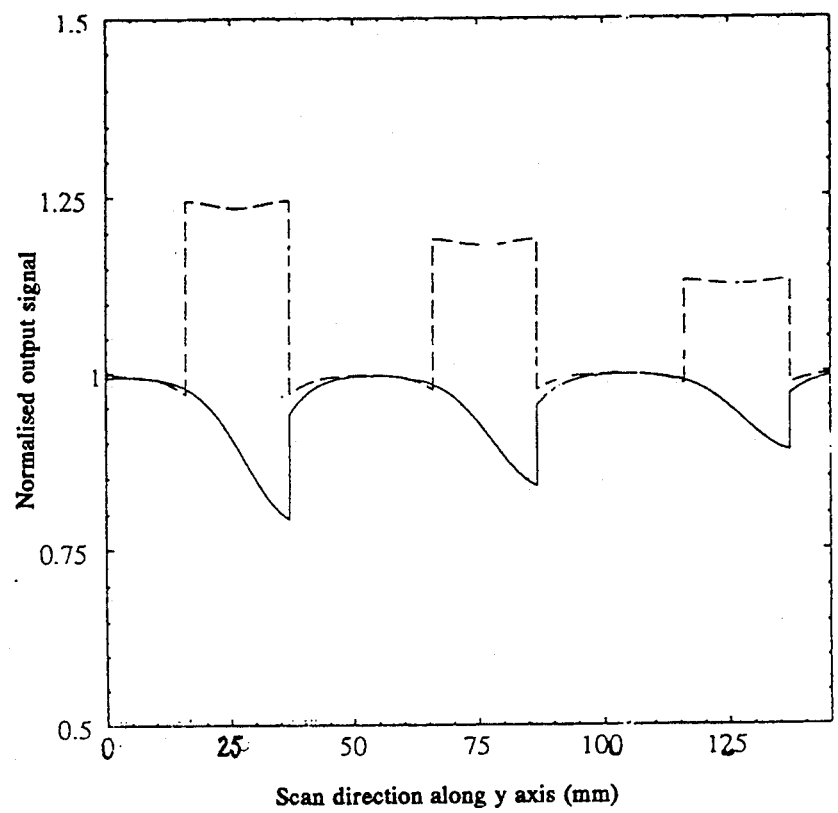
FIG. 14 shows theoretical calculations corresponding to the test yielding the result shown in FIG. 13.

The results of scanning the surface of a mild steel test block containing saw-cut notches of 1 mm, 2 mm, 3 mm, 4 mm and 5 mm depths with the ACFM part of the probe, both before and after the implementation of the compensating coil, are shown in FIG. 12. As these results show, there is a marked improvement in the sensitivity and quality of the signals associated with the notches, when the compensating coil is employed. FIG. 13 shows typical signals from the integrated ACFM-SMFM probe when used to scan a mild steel test block with saw-cut notches of 2 mm, 3 mm and 4 mm depths. These notches were separated by 50 mm and simulated long surface cracks. As the ACFM probe encounters the notches, rectangular pulses are produced as shown in FIG. 13. The detection of each notch by the ACFM technique has been confirmed by the SMFM technique. With the aid of the computer model mentioned above, the crack signals corresponding to both methods have been generated and are shown in FIG. 14 - and there is a good agreement with the experimental results shown in FIG. 13.

What is claimed is:

1. A probe for detecting surface cracks in a workpiece comprising:
   a main frame;
   a pair of substantially U-shaped inducer wires lying in parallel spaced-apart planes and supported by said main frame;
   at least two legs disposed on a bottom portion of said main frame and supporting said main frame at a predetermined height above a workpiece surface wherein lower portions of each of said two inducer wires extend substantially parallel to said surface; and
   a magnetic sensor attached to one of said legs and disposed to lie closely adjacent to the workpiece surface for interrogating a magnetic field induced substantially in the surface of the workpiece by said inducer wires to determine whether surface cracks exist in the workpiece surface.

2. The probe recited in claim 1, wherein each of said legs is resiliently mounted on said main frame.

3. The probe recited in claim 2, wherein each of said legs has a free end provided with a part-spherical ball for contacting the workpiece surface.

4. The probe recited in claim 1, wherein the sensor is mounted within a housing provided on one of said legs at the free end thereof.

5. The probe recited in claim 1 further comprising a compensating coil disposed between and electrically coupled in series with said two legs for compensating effects of extraneous voltages generated by the inducer wires in said two legs.

6. A probe for detecting surface cracks in a workpiece, which probe comprises:

a main frame;

a pair of substantially U-shaped inducer wires lying in parallel spaced apart planes and supported by said main frame for inducing eddy currents in a surface of the workpiece;

two sensing legs for supporting said frame at a predetermined height above the workpiece surface wherein lower portions of each of said two inducer wires are substantially parallel to that surface, and for sensing potential drops resulting from the eddy currents in the surface of the workpiece so that surface cracks in the workpiece can be detected; and a compensating coil disposed between the two legs and electrically coupled in series with said two legs for compensating effects of extraneous voltage generated by the pair of inducer wires.

* * * * *